(12) United States Patent
Bode et al.

(10) Patent No.: US 8,882,722 B2
(45) Date of Patent: Nov. 11, 2014

(54) MEDICAMENT INJECTION DEVICE WITH LOCKOUT FEATURE

(75) Inventors: Andreas Bode, Frankfurt am Main (DE); Paul Edward Jansen, Bridgewater, NJ (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 306 days.

(21) Appl. No.: 13/500,806

(22) PCT Filed: Oct. 8, 2010

(86) PCT No.: PCT/EP2010/065097
§ 371 (c)(1),
(2), (4) Date: Sep. 27, 2012

(87) PCT Pub. No.: WO2011/042540
PCT Pub. Date: Apr. 14, 2011

(65) Prior Publication Data
US 2013/0012885 A1    Jan. 10, 2013

(30) Foreign Application Priority Data
Oct. 8, 2009  (EP) .................................... 09172508

(51) Int. Cl.
*A61M 5/00* (2006.01)
*A61M 5/24* (2006.01)
*A61M 5/315* (2006.01)
*A61M 5/31* (2006.01)
*G01R 31/36* (2006.01)

(52) U.S. Cl.
CPC ............. *A61M 5/24* (2013.01); *A61M 5/31525* (2013.01); *A61M 2005/2407* (2013.01); *A61M 2005/2488* (2013.01); *A61M 2005/2492* (2013.01); *A61M 2005/3125* (2013.01); *A61M 2205/581* (2013.01); *A61M 2205/582* (2013.01); *A61M 2205/583* (2013.01); *G01R 31/36* (2013.01)
USPC .......................................... 604/207; 604/211

(58) Field of Classification Search
CPC ..................... A61M 5/31563; A61M 5/31546; A61M 5/31535; A61M 5/31571; A61M 5/31566; A61M 5/31533; A61M 5/31501; A61M 2005/3125
USPC ................................................ 604/207–211
See application file for complete search history.

(56) References Cited

U.S. PATENT DOCUMENTS

| 6,997,911 B2 | 2/2006 | Klitmose |
| 2004/0062148 A1 | 4/2004 | Skyggebjerg et al. |

FOREIGN PATENT DOCUMENTS

| DE | 19842722 | 4/2000 |
| WO | 99/43283 | 9/1999 |

(Continued)

OTHER PUBLICATIONS

European Search Report for European App. No. 09172508, completed Mar. 25, 2010.
International Search Report for International App. No. PCT/EP2010/065097, completed Feb. 18, 2011.

(Continued)

*Primary Examiner* — Kevin C Sirmons
*Assistant Examiner* — Deanna K Hall
(74) *Attorney, Agent, or Firm* — McDonnell Boehnen Hulbert & Berghoff LLP

(57) ABSTRACT

A lockout feature for an injection device includes a time lock that prevents a user from administering a dose of medicament prior to a pre-determined time interval. The lockout feature can interface with a cap and dose setting module to prevent removal of the cap or it can work to disable the dose delivery module to prevent an injection from occurring.

15 Claims, 1 Drawing Sheet

(56) References Cited

FOREIGN PATENT DOCUMENTS

| WO | 2006/125692 | | 11/2006 |
| WO | WO2006/125692 | * | 11/2006 |

OTHER PUBLICATIONS

International Preliminary Report on Patentability for International App. No. PCT/EP2010/065097, completed Sep. 22, 2011.

* cited by examiner

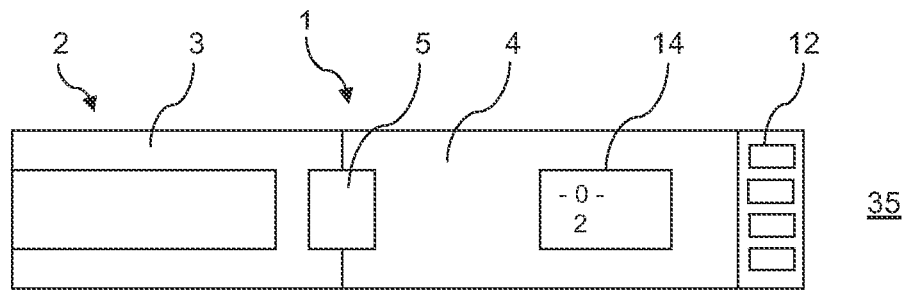
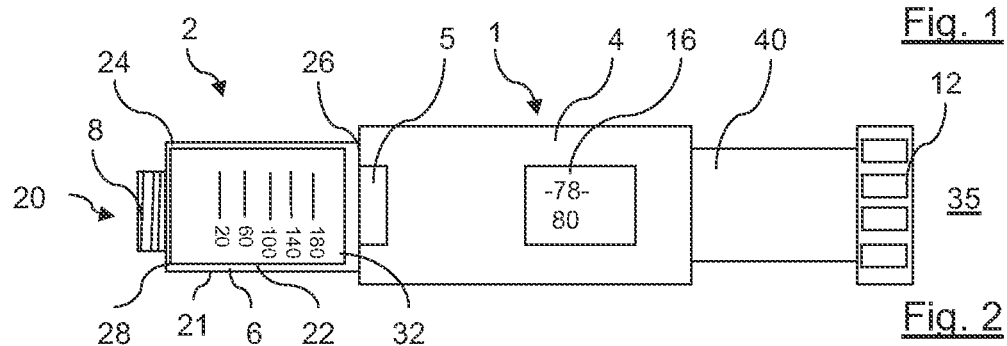
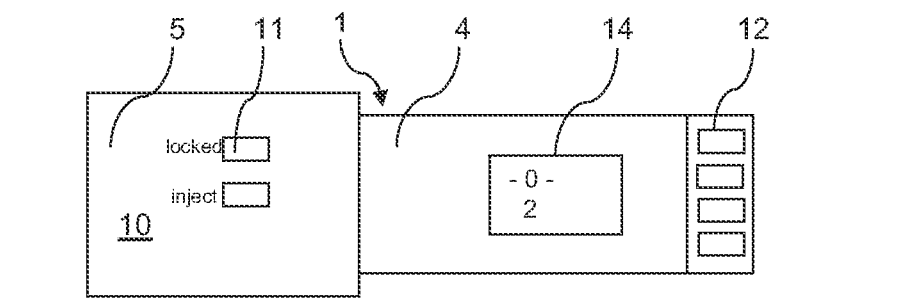
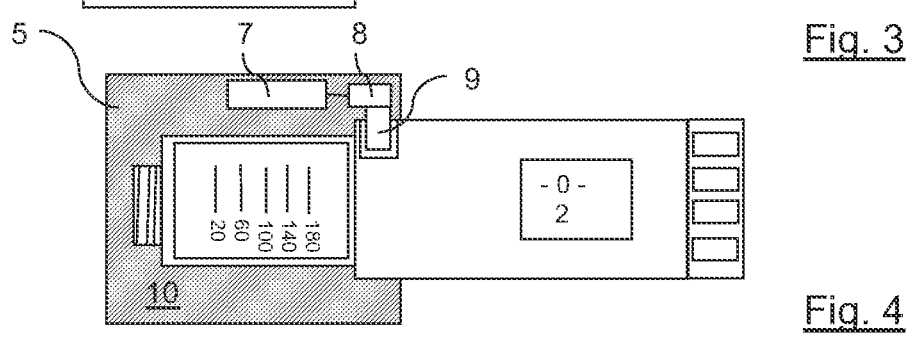

MEDICAMENT INJECTION DEVICE WITH LOCKOUT FEATURE

CROSS REFERENCE TO RELATED APPLICATIONS

The present application is a U.S. National Phase Application pursuant to 35 U.S.C. §371 of International Application No. PCT/EP2010/065097 filed Oct. 8, 2010, which claims priority to European Patent Application No. 09172508.5 filed on Oct. 8, 2009. The entire disclosure contents of these applications are herewith incorporated by reference into the present application.

The present patent application is generally directed to drug delivery devices. More particularly, the present patent application is generally directed to drug delivery devices, such as pen type drug delivery devices. Such devices provide for self-administration of medicinal products from a multi-dose cartridge and permit a user to set a variable delivery dose or set a single fixed dose. In particular, the present invention relates to pen type device that has a time lock that prevents a user from accidental over medication by disabling the pen device.

The present application may find application in both resettable (i.e., reusable) and non-reusable (i.e., non-resettable) type drug delivery devices as well as single dose pre-filled devices. However, aspects of the invention may be equally applicable in other scenarios as well.

Pen type drug delivery devices have application where regular injection by persons without formal medical training occurs. This is increasingly common among patients having diabetes where self-treatment enables such patients to conduct effective management of their disease.

Pen-type injectors are well known and all universally use some form of cartridge capable of delivering multiple doses of a specific type of medicine, such as human growth hormone or insulin. For a number of end users of such devices (typically patients being prescribed medicines) the time interval between injections may be many hours or in some cases several days. For certain patients, remembering when an injection is next due or when their last injection occurred is a major challenge. Clearly, it is important for such patients to know with absolute certainty when it is safe to perform their next scheduled injection. This is especially true for elderly patients, particularly for those who are advanced in age or mentally impaired.

Manufacturers of other pen type devices have suggested modular pen devices where replaceable modules can be added to the pen to perform different notification functions for a specific patient.

Such a system is disclosed in U.S. Pat. No. 6,997,911. Likewise, WO 2006/125692 describes a notice feature that alerts the user if a second dose is attempted before a set time period passes from the first dose, however, there is no teaching that any part of the device is locked if the user attempts to administer the second dose before the pre-set time period expires. Additionally, WO 99/43283, although it does mention a locking mechanism, it does not lock the pen cap to the dose dial housing as in the pending application. In summary, these prior notification systems fail to describe any means to actually prevent a user from performing an injection before it is safe to do so.

Accordingly, there still exists a strong need to provide users of such devices with a simple and easy to use injection device that will prevent premature injection.

Our invention provides a solution to these problems by providing an automatic lockout feature in the injection device so that certain users will be prevented from accidental over medication. These and other advantages will become evident from the following more detailed description of the invention.

According to an exemplary arrangement, our invention covers a safety injection system comprising, in combination, a multi-dose delivery module having a distal end for accepting a needle and a proximal end for setting a dose. The distal end is configured to accept a removable cap that covers the needle and which has associated therewith a lockout feature that prevents a user from administering an injection unless predetermined conditions exist. This lockout feature preferably comprises a time lock that forms an interface with the multi-dose delivery module such that when in the locked mode the cap cannot be removed from the device.

The time lock can be of any mechanical and electrical design that can conveniently be integrated into a pen type injection device. Preferably it will be an electromechanical design, such as a solenoid that is capable of opening a mechanical latch, key, snap lock, sliding lock, electromagnetic, biasing means or other mechanism that will create an interface between the cap and the dose delivery module.

Alternatively, the lockout feature can be located in the dose delivery module and work to prevent a dose from being set or an injection from being effected. As the name implies the lock can be settable, directly on the device or wirelessly from a remote location, it can open or close at a specific time of day, or day of the week, or week of a month.

The time lock is preferably operated by a controller that can be part of the multi-dose delivery module or part of the cap.

The controller can be configured to receive a signal from an electronic circuit where the received signal is through a wired connection or wireless connection.

The electronic circuit itself can be part of cap, the multi-dose delivery module, a personal computer, a remote computer, a remote server, or can be part of a combination of these items.

It is preferred that the controller is programmable and particularly preferred that it is capable of being pre-programmed by a user of the safety injection system or by a health care professional.

Preferably the electronic circuit is part of the time lock, which is placed in a cradle and connected to a health care professional's computer. The health care professional can then program the time lock with a specific instructions of when the lock will open to allow for an injection, how long to remain locked until the next injection, when to provide reminders to the patient, when to transmit data relating to the injection activity back to the health care professional, and like activities tailored to a treatment regime.

In one embodiment the controller is pre-programmed with an algorithm that defines a therapeutic treatment regime. This may preferably be developed for a general class of patients suffering from a particular disease state or preferably developed for a specific individual patient.

The safety injection system of our invention can also include an alert sub-system in communication with the controller, preferably where the alert sub-system is configured to provide a user of the safety injection device with an audible, mechanical vibration, visual, or combination of these signals to provide a reminder to the patient that the device is unlocked and that it is time to perform an injection.

In an alternate embodiment of our invention the time lock is operatively connected only to the multi-dose delivery module such that the drive mechanism of the device is locked out to prevent a user from administering a dose at the incorrect time. As with the previous embodiment the time lock is settable and can be opened and closed by a controller, which itself can be located in the dose delivery module or the cap. The controller can of course be configured and program as previously described.

In any of the embodiments of our invention it is possible to have the controller in communication with an analytical device that is configured to monitor or test a physiological characteristic of a user of the safety injection system. An example of such an analytical device would be a blood glucose analyzer.

These as well as other advantages of various aspects of the present invention will become apparent to those of ordinary skill in the art by reading the following detailed description, with appropriate reference to the accompanying drawings.

In a further preferred embodiment, the safety injection system is configured to permanently close the time lock after a preset or settable time. This may be used to prevent injection of medicament after exceeding the expiry date of the medicament to be injected.

The expiry date may in one preferred embodiment be implemented as an absolute value which may be stored in any suitable electronic means of the injection device.

Alternatively or additionally, the expiry date may be implemented as a count down which may preferably finish at or near the expiry date.

"Expiry date" with respect to the invention may preferably be a fixed date in time starting from the production of the medicament and/or a variable date starting from the first injection of the medicament.

In a preferred embodiment, both dates are taken into account so that two dates are stored or storable in any suitable electronic means, one date correlated to the production date and one date correlated to the date of first usage.

The safety injection system may in another preferred embodiment comprise an energy supply for actuating the time lock, wherein the safety injection system is configured to open the time lock when the energy left in the energy supply underruns a set threshold. With this feature it can be secured that the drug delivery device will not be blocked due to an empty energy supply.

One preferred embodiment of this may comprise means for detection the amount of energy left in the energy supply which are functionally connected to the time lock in such. The functional connection may be established via said controller, which uses the information and/or signal from the detection means to unlock the time lock if said threshold is underrun.

An alternative embodiment may comprise an electrical energy supply with a time lock which automatically opens when the current and/or the voltage of the electrical energy supply underruns a certain threshold.

Exemplary embodiments are described herein with reference to the drawings, in which:

FIG. 1 illustrates an arrangement of the drug delivery device in accordance with one aspect of the present invention;

FIG. 2 illustrates the device of FIG. 1 with the protective cap removed to reveal the cartridge holder containing a cartridge medicament, where the dial sleeve is extended proximally from the housing in a dose setting condition;

FIGS. 3 and 4 show an alternative embodiment of the lockout feature where the cap is replaced by sleeve 10 that locks to the dose setting mechanism.

Referring to FIG. 1, there is shown a drug delivery device 1 in accordance with a first arrangement of the present invention. The drug delivery device 1 comprises a housing having a first cartridge retaining part 2, and a dose delivery module or dose setting mechanism 4.

The drug delivery device 1 may be a reusable drug delivery device or alternatively a disposable drug delivery device. By disposable device it is meant an injection device that is obtained from the manufacturer preloaded with medicament and cannot be reloaded with new medicament after the initial medicament is exhausted. The device may be a fixed dose or a settable dose, but in either case it is a multi-dose device.

A first end of the cartridge retaining means 2 and a second end of the dose setting mechanism 4 are secured together by connecting features. For disposable devices, these connecting features would be permanent and for reusable devices, these connecting features would be releasable.

The drug delivery device 1 could also include syringes or other devices that have a dial sleeve, plunger, or other setting member that the user translates outwards, pulls or pushes, or cocks, including pre-filled single dose devices.

In this illustrated arrangement, the cartridge retaining means 2 is secured within the second end of the dose setting mechanism 4.

A removable protective cap 3 is releasably retained over a second end or distal end of a cartridge retaining part or cartridge housing 2.

A lockout feature 5 is positioned between the cap 3 and the dose setting mechanism 4 and is configured to time lock the cap 3 to the dose setting mechanism 4 to prevent an authorized injection. This lockout feature 5 can be mechanical or electromechanical and can secure the cap 3 to the dose setting mechanism 4 such that the drug delivery device 1 would have to be physically destroyed in order to remove the cap 3.

FIGS. 3 and 4 show an alternative embodiment of the lockout feature where the cap is replaced by sleeve 10 that locks to the dose setting mechanism. This sleeve 10 would contain the electronic circuit that controls the time lock mechanism. In the embodiment shown, the time lock mechanism could consist of indicator lights 11 that indicate when the device is locked and when it is open to allow an injection. It could also contain an electronic circuit 7 and a connected motor or driver 8 that operates locking pin 9 or similar connector.

Alternatively, the lockout feature can have a failsafe feature such that the user, in certain circumstances, could override the lockout with a series of input signals that would unlock the connection between the cap 3 and the dose setting mechanism 4. These input signals ensure that the user is making a conscious decision to override the lockout feature.

The dose setting mechanism 4 comprises a dose dial grip 12 and a window or lens 14. A dose scale arrangement 16 is viewable through the window or lens 14. To set a dose of medication contained within the drug delivery device 1, a user rotates the dose dial grip 12, which in turn rotates dial sleeve 40 such that a dialed dose will become viewable in the window or lens 14 by way of the dose scale arrangement 16.

FIG. 2 illustrates the drug delivery device 1 of FIG. 1 with cap 3 removed from a distal end 20 of the medical delivery device 1. This exposes the cartridge housing 6. As illustrated, a cartridge 22 from which a number of doses of a medicinal product may be dispensed, is provided in the cartridge housing 6.

Preferably, the cartridge 22 contains a type of medicament that must be administered relatively often, such as once or more times a day. One such medicament is either long acting or short acting insulin or an insulin analog. The cartridge 22 comprises a bung or stopper (not illustrated) that is retained near a second end or a proximal end 32 of the cartridge 22.

The cartridge housing 6 has a distal end 24 and a proximal end 26.

Preferably, the cartridge distal end 24 of the cartridge housing 6 comprises a groove 8 for attaching a removable needle assembly however other needle assembly connection mechanisms could also be used.

If the drug delivery device 1 comprises a resettable device, the cartridge proximal end 26 is removably connected to the dose setting mechanism 4. In one preferred embodiment, cartridge housing proximal end 26 is removably connected to the dose setting mechanism 4 via a bayonet connection. However, as those of ordinary skill in the art will recognize, other types of removable connection methods such as threads, partial threads, ramps and detents, snap locks, snap fits, and luer locks may also be used.

The cartridge housing 6 further comprises an inner end face 28 near the first end or distal end 24 of the cartridge housing 6. Preferably, in order to maintain dose accuracy, the cartridge 22 is pressed up against or abuts this inner end face 28.

As previously mentioned, the dose setting mechanism 4 of the drug delivery device illustrated in FIG. 2 may be utilized as a reusable drug delivery device (i.e., a drug delivery device that can be reset). Where the drug delivery device 1 comprises a reusable drug delivery device, the cartridge 22 is removable from the cartridge housing 6.

The cartridge 22 may be removed from the device 1 without destroying the device 1 by merely having the user disconnect the dose setting mechanism 4 from the cartridge housing 6.

In use, once cap 3 is removed, a user can attach a suitable needle assembly to the groove 8 provided at the distal end 24 of the cartridge housing 6. Such needle assembly may be screwed onto a distal end 24 of the housing 6 or alternatively may be snapped onto this distal end 24. After an injection has been made, the user can replace the replaceable cap 3 to re-cover the cartridge housing 6. Once replaced the time lock 5 will lock the cap to the dose setting mechanism 4 until it is time for the next injection. Preferably, the outer dimensions of replaceable cap 3 are similar or identical to the outer dimensions of dose setting mechanism 4 so as to provide an impression of a unitary whole as illustrated in FIG. 1 when replaceable cap 3 is in position covering cartridge housing 6 when the device is not in use. Preferably the lockout feature 5 is designed so as not to disrupt or to minimize disruption of the unitary whole design.

FIG. 1 shows the device in a zero dose setting position as evidenced by the "0" showing through window 14. In the zero dose position dial sleeve 40 (see FIG. 2) is hidden because it does not extend in the proximal direction away from the outer housing 35. In other words, the only visible part of the dial sleeve is the numbering seen through the window 14. At this zero dose setting position the indicia on the dial sleeve is not visible to the user.

Referring now to FIG. 2, the user has set a dose of 78 units as indicated by the dose numbers seen through window 14. The dial sleeve 40 has moved or translated outwardly in the proximal direction 35 away from the outer housing. To arrive at this position the user started from the zero dose position and began to rotate dose dial grip 12 causing dial sleeve 40 to also rotate and move axially in a proximal direction revealing or exposing more and more of the dial sleeve as the final dose of 78 units was reached.

The dial sleeve 40 can be manufactured as one or more parts that are assembled together such that all the parts move as a unitary part. For example, a distal end portion maybe made of white plastic with black dose numbers or vice versa to provide maximum contrast. Likewise, different materials of construction may be used for each portion for cost or wear and tear considerations. Manufacturing the dial sleeve 40 in separate sections may also make it easier to add dynamic indicia to the most proximal section of the dial sleeve 40 to assist the user in identifying the type of medicine contained in the cartridge 22.

In an alternative embodiment of the invention the lockout feature may be internal to the dose setting mechanism 4 such that it will prevent a user from dialing or setting a dose or from performing an injection. For example, the lockout feature may lock dial sleeve 40 from rotation, thus preventing a user from rotating dial grip 12 and causing sleeve to translate in the proximal direction.

Alternatively, the lockout feature may allow the user to dial a dose by turning the dial grip, but upon pushing the injection button prevents the piston drive means from advancing the piston into the cartridge when the dose button is pushed. This is accomplished by associating the lockout feature with a clutch mechanism that allows the force exerted by user to be transferred to the piston driver responsible for advancing the piston rod in the distal direction.

As with the previously described lockout feature, this embodiment could use a settable, pre-programmed, computer controlled time lock position inside the outer housing of the dose setting mechanism 4.

The time lock could be mechanical or electromechanical. The lock can be permanent until the next scheduled injection time or it can be overridden by the user following the input of select signals to ensure unlocking of the device is a deliberate act.

The devices of our invention can also contain the necessary mechanical and electrical parts to send a signal to the user to indicate when the device is in the locked or unlocked state. Such signals can be through the use of lights, sounds, or mechanical vibrations.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A safety injection system comprising,
a multi-dose delivery module having a distal end for accepting a needle and a proximal end for setting a dose;
a removable cap configured to cover the distal end of the dose delivery module; and
a time lock operatively connected to the cap and the multi-dose delivery module
where the time lock is configured such that when the cap is placed on the distal end of the dose delivery module after a first injection,
the time lock prevents a user from removing the cap to perform a second injection unless predetermined conditions exist.

2. The safety injection system according to claim 1 where the time lock is time controlled.

3. The safety injection system according to claim 1 where the time lock is settable.

4. The safety injection system according to claim 1 where the time lock is opened and closed by a controller.

5. The safety injection system of claim 4 where the controller is part of the multi-dose delivery module or part of the cap.

6. The safety injection system according to claim 5 where the controller is configured to receive a signal from an electronic circuit.

7. The safety injection system of claim 6 where the signal can be wired or wireless.

8. The safety injection system according to claim 6 where the electronic circuit is part of cap, the multi-dose delivery module, a personal computer, a remote computer, a remote server, or a combination of same.

9. The safety injection system according to claim 4 where the controller is programmable.

10. The safety injection system according to claim 4 further comprising an alert sub-system in communication with the controller.

11. The safety injection system of claim 10 where the alert sub-system is configured to provide a user of the safety injection device with an audible, visual or tactical or combination audible/visible, audible/tactical or visual/tactical signal.

12. The safety injection system according to claim 4 where the controller is in communication with an analytical device that is configured to monitor or test a physiological characteristic of a user of the safety injection system.

13. The safety injection system according to claim 7 where the lock has an override feature to allow a user to unlock the device after inputting one or more predetermined signals into a controller.

14. The safety injection system according claim 1, wherein the safety injection system is configured to permanently close the time lock after a set or settable time.

15. The safety injection system according to claim 1 with an energy supply for actuating the time lock, wherein the safety injection system is configured to open the time lock when the energy left in the energy supply underruns a set threshold.

* * * * *